United States Patent
Calhoun et al.

(10) Patent No.: US 11,365,372 B1
(45) Date of Patent: Jun. 21, 2022

(54) HUNTING SCENT ELIMINATOR

(71) Applicant: Texas Raised Hunting Products LLC, Richmond, TX (US)

(72) Inventors: Bradley A Calhoun, Frankfort, OH (US); Brett A Andrews, Sugarland, TX (US)

(73) Assignee: Texas Raised Hunting Products LLC, Richmond, TX (US)

( * ) Notice: Subject to any disclaimer, the term of this patent is extended or adjusted under 35 U.S.C. 154(b) by 0 days.

(21) Appl. No.: 17/175,685

(22) Filed: Feb. 14, 2021

Related U.S. Application Data

(60) Provisional application No. 62/977,237, filed on Feb. 15, 2020.

(51) Int. Cl.

| | | |
|---|---|---|
| *C11D 3/00* | (2006.01) | |
| *C11D 3/10* | (2006.01) | |
| *C11D 3/12* | (2006.01) | |
| *C11D 17/00* | (2006.01) | |
| *C11D 17/06* | (2006.01) | |
| *C11D 11/00* | (2006.01) | |
| *A01N 59/16* | (2006.01) | |
| *A01N 59/06* | (2006.01) | |
| *C11D 11/02* | (2006.01) | |

(52) U.S. Cl.
CPC ............. *C11D 3/0068* (2013.01); *C11D 3/10* (2013.01); *C11D 3/128* (2013.01); *C11D 11/0017* (2013.01); *C11D 11/0094* (2013.01); *C11D 11/02* (2013.01)

(58) Field of Classification Search
None
See application file for complete search history.

(56) References Cited

U.S. PATENT DOCUMENTS

| | | | |
|---|---|---|---|
| 6,827,874 B2 * | 12/2004 | Souter | C02F 1/5263 424/407 |
| 7,328,789 B2 | 2/2008 | Bohanan, Jr. et al. | |
| 8,066,939 B2 | 11/2011 | Elrod | |
| 8,257,648 B2 | 9/2012 | Elrod | |
| 2002/0090317 A1 * | 7/2002 | Hardy | A61L 9/16 422/5 |
| 2007/0269402 A1 * | 11/2007 | Johnson | A61L 9/145 424/76.2 |
| 2010/0107991 A1 * | 5/2010 | Elrod | G01N 33/0004 422/5 |
| 2014/0178255 A1 | 6/2014 | Elrod | |
| 2017/0142958 A1 | 5/2017 | McDaniel et al. | |
| 2018/0010071 A1 | 1/2018 | Fox | |
| 2018/0133353 A1 * | 5/2018 | Garcia | A61Q 15/00 |
| 2018/0193510 A1 * | 7/2018 | Hitchcock | A61L 9/012 |
| 2018/0289848 A1 * | 10/2018 | Hitchcock | A61L 9/012 |
| 2018/0368401 A1 * | 12/2018 | Swamy | D06M 13/352 |

FOREIGN PATENT DOCUMENTS

KR   20070078426 A * 8/2007

* cited by examiner

*Primary Examiner* — Lorna M Douyon
(74) *Attorney, Agent, or Firm* — Technology Law PLLC; Karen L. Kimble

(57) ABSTRACT

A human odor eliminating composition is described having as ingredients silver water, zeolite, activated carbon and ozone and optionally sodium bicarbonate. The composition can be used as a concentrate or diluted with water for various applications, such as a spray, wipes, or liquid use. The composition can also be a dry powder. It can be used as an additive in soaps, detergents, hand sanitizers, and even on hunting equipment such as tents, gun cases, bags and more.

12 Claims, No Drawings

HUNTING SCENT ELIMINATOR

FIELD OF THE INVENTION

This invention relates to the hunting of game animals, especially white tail deer, using a composition that reduces or even eliminates human scent such that the animal does not realize a hunter is present. This composition can also be used for fishing equipment and fishermen's clothing and equipment where removing human scent is desired.

BACKGROUND OF THE INVENTION

Description of Related Art

Hunters are always trying to find their quarry, often deer, elk, hog or other land animals, desired as game. Many hunters wander around hoping to encounter the desired animal, or they try to study the animals' habits to determine where they would likely be, or they put out bait to have the desired animal feed at the spot with the bait where they can monitor the times they appear. These techniques are only marginally useful and can take a lot of time to have happen. In part because the animals have a keen sense of smell and hearing and can tell when the odor or sounds of a human are near. This smell or noise makes them nervous and they will avoid the areas that they may otherwise have occupied.

Many techniques and devices have been tried to eliminate or mask human odors from hunters in order to increase their ability to find their game animals. A small sample of such methods and devices is provided below, but there are many others.

U.S. Pat. No. 7,328,789, issued Feb. 12, 2008, describes a camouflage bag to store clothing that hunters wear with a means for preventing odors from entering the interior of the bag—useful when the clothes have been washed with a soap to remove human odors—or for preventing odors from leaving the interior of the bag—useful for storing the hunting clothing after wearing by a hunter to minimize the odor. Thus, this patent is an example of a physical barrier to the odor being detected by the animal. A drawback to this method is the human odor will return from sweat from the hunter seeping into the clothing or on the skin when he is out in the field or woods for any length of time hunting.

U.S. Pat. No. 8,066,939, issued Nov. 29, 2011, describes a complex system for removing or lessening human odor while hunting by use of a generator as a device worn on the hunter's back that produces a descending material by blowing the material around the hunter, somewhat like a fog around the hunter, to remove the human odor. This device may include an optional directional apparatus to know which way the wind is blowing to direct the descending material so the hunter is downwind from the animal. This device requires the hunter to wear this device and it must blow the material so there is noise with it that the animal can hear and detracts from its use. Also, as the hunter moves around the field or woods the ability to have the descending material where the hunter is located is an issue as the device is on his back and does not envelope all of him with this material as he moves. This also bulky and cumbersome for the hunter.

U.S. Pat. No. 8,257,648, issued Sep. 4, 2012, addresses the human odor from a hunting blind. The blind described has the ability to have ozone from an ozone generator within the blind produce descending particles that blow through the vented blind to mask the human odor from the hunter inside the blind. This blind construction can be costly, somewhat difficult to assemble on site, and create noise from the generator that the animal can hear. Also, the hunter is breathing the air inside the blind so that some of the descending particles could pose health issues to the hunter when he remains inside the blind for a length of time.

US Pub. Patent Appln. 2014/0178255, published Jun. 26, 2014, describes the use of ozone in the field where a portable ozone generator blows directly onto the hunter and the hunting equipment to eliminate human odor. This device requires that the hunter move the generator as he changes location and he must remain in the area where the ozone is dispensed to have any effect. This device limits the ease of movement of the hunter.

US Pub. Patent Appln. 2017/0142958, published May 25, 2017, describes a scent masking kit where an airtight package contains scent masking gloves and shoe covers to be worn in the hunting area with wipes to use on contact surfaces and a pad for use on the ground. These items have a scent masking material on their exterior surface and are intended to be discarded after leaving the hunting area. These items have a short life span and can be affected by the weather conditions such as rain, dew, sun and other similar factors.

US Pub. Patent Appln. 2018/0010071, published Jan. 11, 2018, describes a method of treating clothes to reduce human odor. Many such soaps, detergents and treatments have been tried. These treatments often do not last long enough for the time of a hunt in the field and when the hunter sweats during the hunting speeds its ineffectiveness as the human odor increases.

Some of the present commercial items hunters buy to eliminate odors are spray on liquid products to remove human odor, but they must be carried and reapplied frequently when the hunter sweats or they otherwise dissipate from the clothing or skin. Examples of such products are Scent A Way (The Hunters Specialty Company), Scent Killer/Scent Killer Gold (Wildlife Research Company), and Control Freak (Primos Company).

Clearly, finding a way to more easily eliminate human odor while hunting in the field that is reproducible, available in sufficient quantities, and at low cost while not having to carry devices that restrict the hunter's movement or produce sounds is desired.

BRIEF DESCRIPTION OF THE INVENTION

This invention provides a composition that effectively eliminates human odor, a process for making the composition, and a method for its use.

The present invention comprises a composition as a concentrate that has as ingredients:
  About 1 gallon (3.8 L) silver water concentrated at 110 ppm to 150 ppm, with 110 ppm preferred
  About from 30 lbs to 75 lbs. sodium bicarbonate, with about 50 lbs. (22.7 Kg) preferred (optional)
  About 2 to about 7 tbsp. of zeolite (the finest grind available), preferred 4 tbsp. (60 g)
  About 1 to 5 tsp. of activated carbon, preferred 2 tsp. (8 g)
  Ozone These components may be scaled up or down so long as the relative ratios of each component in the total composition are maintained. The amounts of each component above can be varied by about ±10% from the preferred amounts. The ingredients are selected within the stated ranges above to equal 100% by wt. of the final concentrate.

The process makes the silver water, as described below, and then the zeolite and activated carbon are added to it. The resulting solution is treated for at least 25 minutes to 48 hours with ozone. Then, when a dry powder is prepared, the sodium bicarbonate is added last to the composition and mixed until dry. The ozone reacts with the components to make a composition and also makes the composition sterile. The final composition is a dry powder which can be bottled or put into any container. Thus, large batches can be made or individual amounts to carry when hunting.

The present dry concentrate of about 2 to 6 oz., preferred 4 oz., can be diluted with about 128 oz. of water to make a liquid or spray or put into a wipe that is moist for application. Also, if a concentrated liquid is desired in place of the dry powder, then the sodium bicarbonate can be omitted.

The present compositions can be used in many ways to eliminate human odor, including but not limited to products such as laundry detergent, bar soap, liquid concentrate, which treats clothes worn by the hunter both by laundry of the items and then applying when in the field or woods when hunting to remove odor from sweat. This composition can even be used to wash down the hunting equipment, including but not limited to gun cases, arrow quivers, tents, blinds, tree stands, or any desired object used by the hunter to remove his scent when hunting.

DETAILED DESCRIPTION OF THE INVENTION

It is understood that the terminology used herein is for the purpose of describing particular embodiments only and is not intended to be limiting. As used in this specification, the singular forms "a", "an", and "the" include plural referents unless the content clearly indicates otherwise. The following terms in the Glossary as used in this application are to be defined as stated below and for these terms, the singular includes the plural.

Various headings are present to aid the reader, but are not the exclusive location of all aspects of that referenced subject matter and are not to be construed as limiting the location of such discussion.

Also, certain US patents and published applications have been incorporated by reference. However, the text of such patents is only incorporated by reference to the extent that no conflict exists between such text and other statements set forth herein. In the event of such conflict, then any such conflicting text in such incorporated by reference US patent or published application is specifically not so incorporated in this patent.

Glossary

DI water means distilled water that tests at 0 ppm for silver
g means gram
Kg means kilogram
L means liter
lbs. means pounds
oz. means ounce
pm means picometer
ppm means parts per million
tbsp. means tablespoon
tsp. means teaspoon Although the present components are used within ranges to provide the formulation, the use of ozone reacts with these components and forms a composition. While not wishing to be bound by theory, it is believed that the components of this formulation are chemically reacted with the ozone, thereby forming a distinct product that provides the desired properties. The precise chemical structure of this composition has not yet been determined.

The process starts by immersing silver rods in DI water (1 gallon) in a colloidal silver generating kit. The silver and DI water are treated for about 24 hours prior to use at about 27 volts. The silver is colloidal in the DI water. The amount of silver in the DI water is at least 110 ppm. If needed such process is continued until the amount of silver meets or exceeds 110 ppm. It is not for human consumption. This ingredient is referred to herein as "silver water". Then Zeolite (4 tbsp; 60 g) and activated carbon (2 tsp; 8 g) are mixed together. The mixture is then added to 1 gallon (3.79 L) of silver water. The mixture is then treated 25 minutes with ozone, but can be treated for 48 hours if desired, using the ozone generator to form the composition. The resulting solution is then combined with 50 lbs. (22.68 Kg) of sodium bicarbonate and mixed until dry. The process makes about 50 lbs (22.68 Kg) of the dry mixture concentrate.

The dry formulation can be used to make various products to eliminate human odor including but not limited to body and hair wash products, bar soap, laundry detergent, lotion, hand sanitizer, and other similar products. Other hunting related uses have also been found such as an odor remover of dead animal smells for taxidermy and tanneries of animal hides and velvet antlers, as well as hunting equipment e.g., hunting blinds, tents, gun cases, quivers, or any item desired to remove human scent.

This invention will be further clarified by a consideration of the following numbered examples which provides the preparation of compositions of this invention, which are intended to be purely exemplary of the present invention.

Materials used in these examples are as follows:

Activated charcoal powder is derived from Bulk herbs and wholesale foods and is food grade and finely ground Borax is from Henkel Corporation as the 20 mule team borax brand DI water is distilled water that tests at 0 ppm for silver Lard is purchased in food stores from the Morrell company Lye (NaOH) is from Santeen company Ozone generator—Sterhen model A-181

Silver generator—Original Silver Generator from The Silver Lining Company as a kit and silver rods that are 12 gauge wire, 99.9% pure that makes colloidal silver; or Kaime Naturals, a prepared colloidal silver water, from Naturally Sourced Sodium bicarbonate ($NHCO_3$) from FP&S Company (Food Products and Services Company) of animal feed grade with 27% sodium Zeolite Clinoptilolite™ from the Heiltropen company as 90-92% activated ultrafine micronized ground (<20 pm), pharmaceutical grade

Example 1: Preparation of Silver Water

Silver water is made by immersing silver rods in DI water in a colloidal silver generating kit. The silver and DI water are treated for 24 hours prior to use at about 27 volts. The silver is colloidal in the DI water. The amount of silver in the DI water is at least 110 ppm. It is not for human consumption.

Example 2: Preparation of a Concentrate Composition

The Zeolite (4 tbsp; 60 g) and activated carbon (2 tsp; 8 g) are mixed together. The mixture is then added to 1 gallon (3.79 L) of silver water (prepared by Example 1). The mixture is then treated 25 minutes with ozone where the ozone reacts with the other components to form the composition. The resulting solution is then combined with 50 lbs. (22.7 Kg) of sodium bicarbonate and mixed until dry. The process makes about 50 lbs. (22.7 Kg) of the dry mixture concentrate.

Example 3: Laundry Detergent

The concentrate from Example 2 is mixed in equal parts by weight with Borax. This is a dry mix with the amount determined by the amount of the two ingredients. It is used in standard washing machines for removing the human odor from hunter's clothing.

Example 4: Bar Soap

Lye (NaOH) (4.25 oz.; 120.5 g) is added to 12 oz. (12 mL) of DI in a stainless-steel container. Lard (32 oz.; 907 g) is melted and added to the lye with an immersion blender slowly. Then 4 oz. (113.4 g) of the concentrate from Example 2 is added to the mixture and stirred until well blended. The mixture is poured into 4 oz. bar molds. The batch makes about 32 bars.

Example 5: Body Wash

Combine 4 tsp. (16 g) of zeolite with 1 tsp. (4 g) of activated carbon and add to 16 oz. (454 g) of silver water (prepared by Example 1) and mix thoroughly. Add this mixture to 1 gallon (3.79 L) of unscented body wash base with an immersion blender. Yields about 144 oz. (4.26 L) of body wash.

Example 6: Scent Barrier

Mix thoroughly 2 tsp. (8 g) of activated carbon, 1 tsp. (4 g) of zeolite and 10 lbs. (4.5 Kg) of concentrate from Example 2. This makes about 10 lbs. (4.5 Kg) of dry mixture. The resulting product is mixed with water and the clothes are immersed in this solution and allowed to air dry.

Example 7: Field Trial

To show how the compositions worked when hunting, Larry Weishuhn, a well-known and respected, famous hunter, agreed to try this product on a hunt. He went hunting pronghorn after he sprayed down his clothing before leaving camp with the present composition. Larry decided to try something very difficult; namely, he went into a broad opening where there was nothing taller than 10 inches of growth to hide behind. Larry stood upright and stalked a pronghorn from over 500 yards away and walked toward him until he was about 12 steps away from him. The pronghorn looked his way but did not seem to see Larry at all, was not spooked and did not run off. Larry said that normally the pronghorn would have spooked immediately and not have let him get within 200 yards before running off. It was amazing. Larry captured this on film as he films many of his hunts.

Clearly, the composition worked for Larry and he was amazed how well.

Although the invention has been described with reference to its preferred embodiments, those of ordinary skill in the art may, upon reading and understanding this disclosure, appreciate changes and modifications which may be made which do not depart from the scope and spirit of the invention as described above or claimed hereafter. Accordingly, this description is to be construed as illustrative only and is for the purpose of teaching those skilled in the art the general manner of carrying out the invention.

The invention claimed is:

1. A composition comprising the following components:
   a) about 1 gallon or about 3.8 L silver water concentrate having at least 110 ppm of silver,
   b) optionally about from 30 lbs. to 75 lbs. sodium bicarbonate,
   c) about 2 to about 7 tbsp. or about 30 g to about 105 g of zeolite,
   d) about 1 to 5 tsp. or about 4 g to 20 g of activated carbon, and
   e) ozone.

2. The composition of claim 1 comprising the following components:
   a) about 1 gallon or about 3.8 L silver water concentrate having at least 110 ppm of silver;
   b) optionally about 50 lbs. or about 22.7 Kg sodium bicarbonate;
   c) about 4 tbsp. or about 60 g of zeolite;
   d) about 2 tsp. or about 8 g activated carbon; and
   e) ozone.

3. The composition of claim 1 wherein the zeolite is finely ground.

4. The composition of claim 1 wherein sodium bicarbonate is present and the composition is a dry powder.

5. The composition of claim 1 wherein the sodium bicarbonate is absent and the composition is a liquid.

6. The composition of claim 2 wherein the amount of the components may vary by about ±10% by wt. and the relative ratios of each component to the other components remain constant within any variation.

7. A process for preparing a composition according to claim 2 comprising:
   a) immersing silver rods in 1 gallon or 3.8 L of distilled (DI) water in a colloidal silver generating kit for 24 hours prior to use at about 27 volts, wherein after the generation the amount of silver in the DI water is at least 110 ppm;
   b) mixing 4 tbsp. or 60 g zeolite and 2 tsp. or 8 g activated carbon and activated carbon (2 tsp; 8 g) with stirring;
   c) adding the mixture from step b) to the silver water of step a) with stirring;
   d) treating the mixture from step c) for about 25 minutes with ozone using an ozone generator to form a liquid composition; and
   e) optionally adding 50 lbs. or 22.7 Kg of sodium bicarbonate to the liquid composition of step d) and mixing until dry providing about 50 lbs or about 22.68 Kg of the dry mixture concentrate.

8. The process of claim 7 wherein the amounts of each ingredient can be varied by ±10% by wt.

9. A method for eliminating human odor comprising treating a hunter's clothing or equipment with a composition according to claim 1 prior to or during hunting.

10. The method of claim 9 wherein the hunter applies the composition as a powder or sprays as a liquid onto his/her clothes or skin while in the field or woods.

11. The method of claim 9 wherein the hunter applies the composition to his/her hunting equipment.

12. The method of claim 11 wherein the hunting equipment is a gun case, tent, blind, or quiver.

* * * * *